(12) United States Patent
Ammerlaan (10) Patent No.: US 9,119,368 B2
(45) Date of Patent: Sep. 1, 2015

(54) LETTUCE VARIETY 41-122 RZ

(75) Inventor: Adrianus Martinus Jozef Ammerlaan, Aramon (FR)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 453 days.

(21) Appl. No.: 13/483,079

(22) Filed: May 30, 2012

(65) Prior Publication Data

US 2012/0311733 A1    Dec. 6, 2012

Related U.S. Application Data

(60) Provisional application No. 61/492,929, filed on Jun. 3, 2011.

(51) Int. Cl.
*A01H 5/12* (2006.01)

(52) U.S. Cl.
CPC .................................. *A01H 5/12* (2013.01)

(58) Field of Classification Search
None
See application file for complete search history.

(56) References Cited

U.S. PATENT DOCUMENTS 8,772,578 B2 *    7/2014    Ammerlaan ................. 800/305

OTHER PUBLICATIONS

IBEB press release "New race of *Bremia lactucae* Bl:27 identified and nominated", May 2010; Plantum NL (Dutch association for breeding, tissue culture, production and trade . . . .

Michelmore R. & Ochoa. O. "Breeding Crisphead Lettuce."In: California Lettuce Research Board, Annual Report 2005-2006, 2006, Salinas, California, pp. 55-68.

Schettini, T.M., Legg, E.J., Michelmore, R.W., 1991. Insensitivity to metalaxyl in California populations of *Bremia lactucae* and resistance of California lettuce cultivars . . . .

Van Ettekoven, K. et al., "Identification and denomination of 'new' races of *Bremia lactucae*," in: Lebeda, A. and Kristkova, E (eds.), Eucarpia Leafy Vegetables, 1999 . . . .

Van der Arend et al. "Identification and denomination of "new "races of *Bremia lactucae* in Europe by IBEB until 2002." In: Van Hintum, Th et al. (eds.), Eucarpia Leafy . . . .

* cited by examiner

*Primary Examiner* — Eileen B O Hara
(74) *Attorney, Agent, or Firm* — Vedder Price P.C.; Thomas J. Kowalski; Deborah L. Lu (57) ABSTRACT

The present invention relates to a *Lactuca sativa* seed designated 41-122 RZ, which may exhibit resistance to downy mildew (*Bremia lactucae* Regel.), and which may have leaves with a solid main vein, narrow base leaves, and thick, strongly blistered, dark green mature leaves. The present invention also relates to a *Lactuca sativa* plant produced by growing the 41-122 RZ seed. The invention further relates to methods for producing the lettuce cultivar, represented by lettuce variety 41-122 RZ.

23 Claims, 2 Drawing Sheets

LETTUCE VARIETY 41-122 RZ

RELATED APPLICATIONS AND INCORPORATION BY REFERENCE

This application which claims priority to U.S. provisional patent application Ser. No. 61/492,929 filed 3 Jun. 2011.

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a new lettuce (*Lactuca sativa*) variety which may be suitable for mechanical harvest and exhibits resistance against downy mildew (*Bremia lactucae*) as well as thick, strongly blistered leaves.

BACKGROUND OF THE INVENTION

Romaine lettuce should provide a product at harvestable stage, which is accepted by processing industry and/or consumers. Therefore the harvestable product should not have tipburn, should have a short core, and it should have thick, strongly blistered leaves with a dark green outer leaf color. Further it should be sufficiently headed, and as a result of this heading provide sufficient yellow-colored heartleaves.

Mature romaine lettuce is mainly harvested by hand. This harvesting process is labor-intensive, and relatively laborer-unfriendly. As it getting more and more costly to hire laborers that want to work outdoor in the field, close to the ground and under all kinds of adverse weather conditions, there is strong interest of the lettuce industry to mechanize this manual harvesting process. However, until now the lack of uniform quality among mature plants is a major problem for mechanical harvest. Poor quality of basal leaves, internal breakdown of heartleaves due to tipburn, fringe burn of leaf margins and fast bolting are the main quality problems. If one would like to mechanize the harvest process, these quality problems result in additional hand sorting, which is costly, and/or a very low net yield, if the plant parts with a high risk of quality problems are mechanically discarded. The latter approach is chosen by some producers that produce romaine hearts, i.e. the intact yellow-green heart of the romaine lettuce without the green outer leaves. For producers that produce romaine lettuce for processing, i.e. pre-washed and pre-cut leaves, this is not feasible because of four major constraints.

The first is the requirement for a mix of green and yellow leaves, which requires the preservation of the undamaged green outer leaves. The second constraint is the strongly reduced net yield, which is a result of the fact that an automated knife should cut through the leaf but not through the core. Especially fast bolting lettuce varieties are unacceptable for mechanized harvest of romaine lettuce for processing purposes because of their long core.

The third constraint is caused by the use of mechanically-driven horizontal knives that easily damage the hollow main veins of romaine leaves and cut halfway through the prostrate, round-shaped, lower outer leaves, which results in wide cut surfaces. Cutting damage on a leaf with a hollow main vein is often not restricted to the cut surface but bruising extends into the leaf along the main vein.

The fourth constraint is the requirement for a leaf to have a good shelf life. This means the leaves should get through the washing and drying process in the factory without bruising or breaking. The leaves should be sufficiently thick and tough to avoid wilting. In addition, the leaves should be strongly blistered to avoid sticking to each other and to the plastic of the packaging, which increases local humidity on the leaf and reduces local respiration.

There exists a need, therefore, for a new type of romaine or cos lettuce, which is suitable for mechanical harvest with a simple horizontal knife and which exhibits resistance against downy mildew (*Bremia lactucae*). The harvested product is meant for processing purposes.

Citation or identification of any document in this application is not an admission that such document is available as prior art to the present invention.

SUMMARY OF THE INVENTION

It is the object of the invention to provide a new type of romaine or cos lettuce, which may be suitable for mechanical harvest with a simple horizontal knife, and which does not have or has reduced problems with downy mildew. The harvested product may be for processing purposes.

The present invention fulfils this need by providing a new romaine, or cos, lettuce (*Lactuca sativa* L. var. *longifolia* Lam) variety, designated 41-122 RZ. Lettuce variety 41-122 RZ which may exhibit a combination of traits including leaves with a solid main vein, narrow base leaves and *Bremia*-resistance, as well as thick, strongly blistered, dark green outer leaves, a short core, absence of fringe burn, and absence of tipburn.

The present invention provides seeds of lettuce cultivar 41-122 RZ, which have been deposited with the National Collections of Industrial, Marine and Food Bacteria (NCIMB) in Bucksburn, Aberdeen AB21 9YA, Scotland, UK and have been assigned NCIMB Accession No. 41832.

In one embodiment, the invention provides a lettuce plant exhibiting a combination of traits including resistance against downy mildew (*Bremia lactucae*), leaves with a solid main vein, narrow base leaves, and thick, strongly blistered, mature leaves, representative seed of which have been deposited under NCIMB Accession No. 41832.

In one embodiment, the invention provides a lettuce plant exhibiting a combination of traits including resistance against downy mildew (*Bremia lactucae*), leaves with a solid main vein, narrow base leaves, thick, strongly blistered, mature leaves, a short core, absence of fringe burn, absence of tipburn, no undulation of the fourth leaf, and very slow bolting, representative seed of which have been deposited under NCIMB Accession No. 41832.

In one embodiment, the invention provides a lettuce plant designated 41-122 RZ, representative seed of which have been deposited under NCIMB Accession No. 41832.

In an embodiment of the present invention, there also is provided parts of a lettuce plant of the invention, including parts of a lettuce plant exhibiting a combination of traits including resistance against downy mildew (*Bremia lactucae*), leaves with a solid main vein, narrow base leaves, and thick, strongly blistered, mature leaves, or parts of a lettuce plant having any of the aforementioned resistance(s) and a combination of traits including one or more morphological or physiological characteristics tabulated herein, including parts of lettuce variety 41-122 RZ, wherein the plant parts are involved in sexual reproduction, which include, without limitation, microspores, pollen, ovaries, ovules, embryo sacs or egg cells and/or wherein the plant parts are suitable for vegetative reproduction, which include, without limitation, cuttings, roots, stems, cells or protoplasts and/or wherein the plant parts are tissue culture of regenerable cells in which the cells or protoplasts of the tissue culture are derived from a tissue such as, for example and without limitation, leaves, pollen, embryos, cotyledon, hypocotyls, meristematic cells, roots, root tips, anthers, flowers, seeds or stems. The plants of the invention from which such parts may come from include those wherein representative seed of which has been deposited under NCIMB Accession No. 41832.

In another embodiment there may be a plant grown from seeds, representative seed of which having been deposited under NCIMB Accession No. 41832. In a further embodiment there may be a plant regenerated from the above-described plant parts or regenerated from the above-described tissue culture. Advantageously such a plant may have morphological and/or physiological characteristics of lettuce variety 41-122 RZ and/or of a plant grown from seed, representative seed of which having been deposited under NCIMB Accession No. NCIMB 41832—including without limitation such plants having all of the morphological and physiological characteristics of lettuce variety 41-122 RZ and/or of plant grown from seed, representative seed of which having been deposited under NCIMB Accession No. NCIMB 41832. Accordingly, in still a further embodiment, there is provided a lettuce plant having all of the morphological and physiological characteristics of lettuce variety 41-122 RZ, representative seed of which having been deposited under NCIMB Accession No. 41832. Such a plant may be grown from the seeds, regenerated from the above-described plant parts, or regenerated from the above-described tissue culture. A lettuce plant having any of the aforementioned resistance(s), a lettuce plant having any of the aforementioned resistance(s) and one or more morphological or physiological characteristics recited or tabulated herein, and a lettuce plant advantageously having all of the aforementioned resistances and the characteristics recited and tabulated herein, are preferred. Parts of such plants—such as those plant parts above-mentioned—are encompassed by the invention.

In one embodiment, there is provided progeny of lettuce cultivar 41-122 RZ produced by sexual or vegetative reproduction, grown from seeds, regenerated from the above-described plant parts, or regenerated from the above-described tissue culture of the lettuce cultivar or a progeny plant thereof, representative seed of which having been deposited under NCIMB Accession No. 41832.

Progeny of the lettuce variety 41-122 RZ may be modified in one or more other characteristics, in which the modification is a result of, for example and without limitation, mutagenesis or transformation with a transgene.

In still another embodiment, the present invention provides progeny of lettuce cultivar 41-122 RZ produced by sexual or vegetative reproduction, grown from seeds, regenerated from the above-described plant parts, or regenerated from the above-described tissue culture of the lettuce cultivar or a progeny plant thereof, in which the regenerated plant shows a combination of traits including resistance against downy mildew (*Bremia lactucae*), leaves with a solid main vein, narrow base leaves, and thick, strongly blistered, mature leaves.

In still a further embodiment, the invention may comprise a method of producing a hybrid lettuce seed comprising crossing a first parent lettuce plant with a second parent lettuce plant and harvesting the resultant hybrid lettuce seed, in which the first parent lettuce plant or the second parent lettuce plant is a lettuce plant of the invention, e.g. a lettuce plant having a combination of traits including resistance against downy mildew (*Bremia lactucae*), leaves with a solid main vein, narrow base leaves, and thick, strongly blistered, mature leaves and one or more morphological or physiological characteristics tabulated herein, including a lettuce plant of lettuce cultivar 41-122 RZ, representative seed of which having been deposited under NCIMB 41832.

In another embodiment, the invention may comprise producing a lettuce plant having a combination of traits including resistance against downy mildew (*Bremia lactucae*), leaves with a solid main vein, narrow base leaves, and thick, strongly blistered, mature leaves comprising: crossing a mother lettuce plant with a father lettuce plant to produce a hybrid seed; growing said hybrid seed to produce a hybrid plant; selfing said hybrid seed to produce F2 progeny seed; selecting said F2-plants for exhibiting a combination of traits including resistance against downy mildew (*Bremia lactucae*), leaves with a solid main vein, narrow base leaves, and thick, strongly blistered, mature leaves.

Advantageously the selfing and selection may be repeated; for example at least once, or at least twice, thrice, four times, five times, six times or more, to produce F3 or F4 or F5 or F6 or subsequent progeny, especially as progeny from F2 can exhibit the aforementioned combination of traits, and can be desirable.

In still a further embodiment, the invention may comprise a method of producing a lettuce cultivar containing a combination of traits including resistance against downy mildew (*Bremia lactucae*), leaves with a solid main vein, narrow base leaves, and thick, strongly blistered, mature leaves.

The invention even further relates to a method of producing lettuce comprising: (a) cultivating to the vegetative plant stage a plant of lettuce variety 41-122 RZ, representative seed of which having been deposited under NCIMB Accession No. NCIMB 41832, and (b) harvesting lettuce leaves or heads from the plant. The invention further comprehends packaging the lettuce plants, heads or leaves.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims, terms such as "comprises", "comprised", and "comprising" and the like (e.g., "includes", "included", "including", "contains", "contained", "containing", "has", "had", "having", etc.) can have the meaning ascribed to them in US Patent law, i.e., they are open ended terms. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. Similarly, the terms "consists essentially of" and "consisting essentially of" have the meaning ascribed to them in US Patent law, e.g., they allow for elements not explicitly recited, but exclude elements that are found in the prior art or that affect a basic or novel characteristic of the invention. See also MPEP §2111.03. In addition, the term "about" is used to indicate that a value includes the standard deviation of error for the device or method being employed to determine the value.

These and other embodiments are disclosed or are obvious from and encompassed by the following Detailed Description.

DEPOSIT

The Deposit with NCIMB Ltd, Ferguson Building, Craibstone Estate, Bucksburn, Aberdeen AB21 9YA, UK, on May 4, 2011, under deposit accession number NCIMB 41832 was made pursuant to the terms of the Budapest Treaty. Upon issuance of a patent, all restrictions upon the deposit will be removed, and the deposit is intended to meet the requirements of 37 CFR §1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION OF THE INVENTION

The invention provides methods and compositions relating to plants, seeds and derivatives of a new lettuce variety herein referred to as lettuce variety 41-122 RZ. Lettuce variety 41-122 RZ is a uniform and stable line, distinct from other such lines.

In a preferred embodiment, the specific type of breeding method employed for developing a lettuce cultivar is pedigree selection, where both single plant selection and mass selection practices are employed. Pedigree selection, also known as the "Vilmorin system of selection," is described in Fehr, W., Principles of Cultivar Development, Volume I, MacMillan Publishing Co., which is hereby incorporated by reference.

When pedigree selection is applied, in general selection is first practiced among $F_2$ plants. In the next season, the most desirable $F_3$ lines are first identified, and then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny from the preceding generation.

Using this pedigree method, two parents may be crossed using an emasculated female and a pollen donor (male) to produce $F_1$ offspring. Lettuce is an obligate self-pollination species, which means that pollen is shed before stigma emergence, assuring 100% self-fertilization. Therefore, in order to optimize crossing, a method of misting may be used to wash the pollen off prior to fertilization to assure crossing or hybridization.

Parental varieties are selected from commercial varieties that individually exhibit one or more desired phenotypes. Additionally, any breeding method involving selection of plants for the desired phenotype can be used in the method of the present invention.

The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

Lettuce variety 41-122 RZ was developed by crossing two varieties, 'Hearts Delight' and 'Actarus', in a glasshouse in Aramon, France, in 2004. The F1 resulting from this cross was grown under protected conditions. A population of F2 seed was obtained through self-pollination. When growing the F2 population in 2005, selection for multiple characteristics was performed, and specifically for *Bremia*-resistance, a solid main vein, and thick, strongly blistered leaves. One F2 plant, 05A.22621 was selected in Aramon, and this plant was self-pollinated to obtain F3 seed, designated 06A.52088.

The F3 seed was sown in Fijnaart, The Netherlands, in 2006, and after a subsequent round of selection for multiple characteristics including *Bremia*-resistance, a solid main vein, and thick, strongly blistered leaves, an F3 plant was selected, namely 06A.71757. The plant was self pollinated and F4 seed, 07A.51705, was produced. Subsequently, the F4 was sown in the field in Tarascon, France, in 2007 as 07A.26116, and an F4 plant was selected from the population after selection for preferred characteristics including *Bremia* resistance, a solid main vein, and thick, strongly blistered leaves. Self pollination was performed, and F5 seed 08A.51674 was produced.

In 2008 (France) and 2009 (The Netherlands) two more rounds of selection to optimize the uniformity of the line were done, resulting in F6 seed 09A.41714 and, after selecting and selfing the F6 plant 09A.71747, an F7 seedlot 10A.40907.

The seed from the F7 line 10R.990238 was established to be uniform, and multiplied in the glasshouse in Fijnaart in 2010, to obtain F8 seed lot 10R.238. 2500 seeds from this seed lot were deposited under Accession No. NCIMB 41832 on May 4, 2011.

In one embodiment, a plant of the invention has all the morphological and physiological characteristics of lettuce variety 41-122 RZ. These characteristics of a lettuce plant of the invention, e.g. variety 41-122 RZ, are summarized in Tables 1-4.

Next to the morphological and physiological characteristics mentioned in Tables 1-4, a plant of the invention also exhibits resistance to downy mildew (*Bremia lactucae* Regel.).

As used herein, resistance against *Bremia lactucae* Regel is defined as the ability of a plant to resist infection by various strains of *Bremia lactucae* Regel. in all stages between the seedling stage and the harvestable plant stage via a hypersensitivity response (Crute, I. R., Annual Rev. Phytopathol., 30:485-506, 1992; incorporated herein by reference). The various strains against which 41-122 RZ exhibits resistance are NL1, NL2, NL4, NL5, NL6, NL7, NL10, NL12, NL13, NL14, NL15, Bl:17, Bl:18, Bl:20, Bl:21, Bl:22, Bl:24, Bl:25, and Bl:26, (Van Ettekoven K, Van der Arend A J M, 1999. In: Lebeda A, Kristkova E (eds.) Eucarpia leafy vegetables '99. Palacky University, Olomouc, Czech Republic, 1999: 171-175; Van der Arend et al., 2003. In: Van Hintum et al. (Eds.) Eucarpia Leafy Vegetables 2003. CGN, Wageningen, the Netherlands 2003: 151; Van der Arend et al., 2006. In: Pink et al. (Eds.) Eucarpia Leafy Vegetables 2006. Warwick HRI, Wellesbourne, UK, 2007 incorporated herein by reference), Ca-V, Ca-VI, Ca-VII, Ca-VIII (Michelmore R. & Ochoa. O. "Breeding Crisphead Lettuce." In: California Lettuce Research Board, Annual Report 2005-2006, 2006, Salinas, Calif., pp. 55-68).

Resistance typically is tested by two interchangeable methods, described by Bonnier, F. J. M. et al. (Euphytica, 61(3): 203-211, 1992; incorporated herein by reference). One method involves inoculating 7-day old seedlings, and observing sporulation 10 to 14 days later. The other method involves inoculating leaf discs with a diameter of 18 mm obtained from a non-senescent, fully grown true leaf and observing sporulation 10 days later.

As used herein, romaine is *Lactuca sativa* L. var. *longifolia* Lam; also known as cos. The plant develops in an upright open or upright compact growing habit with coarse textured leafs. The younger leaves are longer than they are wide, fifteen cupping together to form an elongated loose head. Leaf margins are often entire or undulated, rarely frilled. Outer leaves range in color from light green to dark green. Inner heartleaves are smaller and range from light yellow to light green in color.

Figure 1:
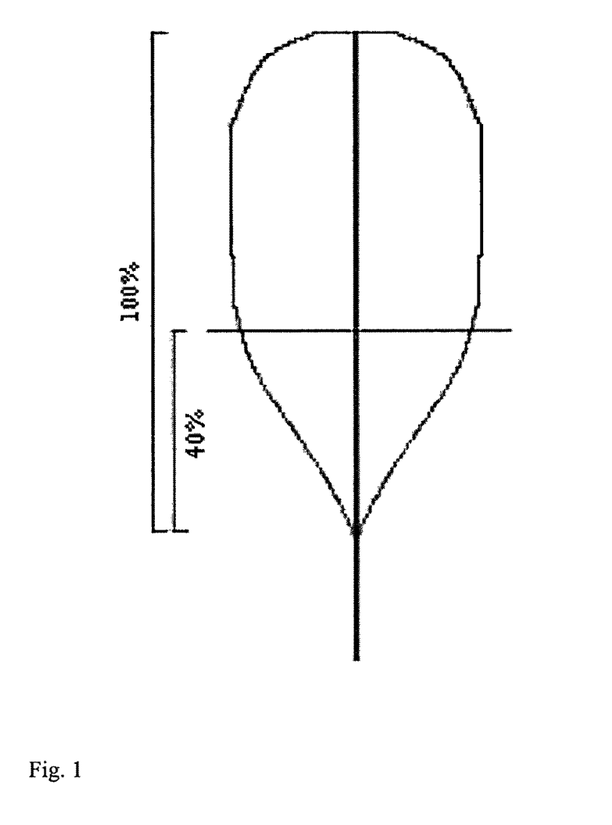
FIG. 1 shows a transverse section at 40% of leaf lamina length to observe solidness of main vein.

As used herein, a solid main vein is the main vein of a fully-grown tenth to fifteenth leaf, which is characterized by the fact that the vein is not hollow, which is observed by visual inspection of a transverse section of the leaf. The transverse section should be made at 40% of the total leaf length, starting from the leaf base (see FIG. 1). For comparison two standard varieties can be used: Maximus, with hollow veins, and Tiberius, with solid veins.

As used herein, a narrow base leaf is characterized by a length/width-ratio of 1.5 or higher. A mature romaine lettuce plant has got narrow base leaves if the average length/width-ratio of the fully-grown tenth to the fifteenth leaf is 1.5 or higher. For comparison two standard varieties can be used: Maximus with broad base leaves, and Chilim with narrow base leaves.

As used herein, dark green outer leaves or dark green mature leaves are defined by the color of a fully-grown tenth to fifteenth leaf, which should be similar to or darker than 137B, 138A, 144A, or 146A on the RHS color chart (The Royal Horticultural Society, London, UK).

As used herein, thick leaves are characterized by a thick, slightly tough leaf texture. For comparison the standard variety "Parris Island" can be used. As used herein, intermediate thick leaves are characterised by a flexible leaf texture, which is less thick than "Parris Island". For comparison the standard variety "Blonde Lente à Monter" can be used.

As used herein, strongly blistered leaves are characterised by a high density of leaf bubbles. For comparison the standard variety "Prize Head" can be used. As used herein moderately blistered leaves are characterised by a intermediate density of leaf bubbles. For comparison the standard variety "Vanguard" can be used.

As used herein, a short core is defined by measuring the length of the core of a harvested mature plant with outer leaves attached. The plant should be grown outdoor under long-day conditions: sowing 5-15 days before the longest day in a mild mid-latitude climate with a warm summer (Köppen-classification: Csb or Cfb; McKnight & Hess, 2000. Physical Geography: A Landscape Appreciation. Upper Saddle River, N.J.: Prentice Hall). A mature plant grown under these conditions is defined as being headed and having a weight of 600-1000 g after harvest. The core of such a plant is defined as 'short' if its length is less than or equal to 8 cm.

As used herein, absence of fringe burn is established by growing plants in outdoor conditions in a winter production area for lettuce with an average daily temperature of the coldest month between 11 and 14 C, for example Cartagena, Spain or Yuma, USA. The growing cycle under these conditions should be at least 16 weeks from sowing a seed to harvesting a mature plant. Harvesting the mature plant should take place in the month after the coldest month. Absence of fringe burn is defined by observing the leaf margin of the tenth until the fifteenth leaf. Absence of fringe burn is established, if for each of these leaves less than 2% of the perimeter of the leaf margin is necrotic.

As used herein, absence of tipburn is established by growing plants in outdoor conditions in spring conditions in a winter production area for lettuce with an average daily temperature of the coldest month between 11 and 14 C, for example Cartagena, Spain or Yuma, USA. Harvesting the mature plant should take place in the third month after the coldest month. Absence of tipburn is defined by observing the ten most recently developed heart leaves longer than 5 cm. Absence of tipburn is established, if for each of these leaves less than 1% of the perimeter of the leaf margin is necrotic. The additional requirement for establishing absence of tipburn is that the comparison variety Maximus, grown under the same conditions with the same sowing and harvest date, shows presence of tipburn, and a second comparison variety Optimus, grown under the same conditions with the same sowing and harvest date, shows absence of tipburn. Presence of tipburn is established, if for at least one out of the ten most recently developed heart leaves longer than 5 cm, at least 1% of the perimeter of the leaf margin is necrotic.

Embodiments of the inventions advantageously have one or more, and most advantageously all, of these characteristics.

In Table 1 that follows, the traits and characteristics of the *Lactuca sativa* L. var. *longifolia* Lam romaine lettuce plant having the designation 41-122 RZ, are given compared to the mentioned comparison varieties, referred to as "Tiberius", "Maximus", "Optimus", and "Chilim".

TABLE 1

| Character | "41-122 RZ" | "Tiberius" | "Maximus" | "Optimus" | "Chilim" |
|---|---|---|---|---|---|
| Type | romaine or cos | romaine or cos | romaine or cos | romaine or cos | romaine or cos |
| hollow/solid main vein | solid | solid | hollow | hollow | hollow |
| broad/narrow base leaves | narrow | broad | broad | broad | narrow |

TABLE 1-continued

| Character | "41-122 RZ" | "Tiberius" | "Maximus" | "Optimus" | "Chilim" |
|---|---|---|---|---|---|
| blond/dark green color | dark | dark | dark | blond | blond |
| core length | short | long | short | short | long |
| tipburn | absent | present | present | absent | present |
| fringe burn | absent | absent | absent | present | present |

In the Tables that follow, the traits and characteristics of the *Lactuca sativa* L. var. *longifolia* Lam romaine lettuce plant referred to as "41-122 RZ" are given, compared to the most similar variety, referred to as "Actarus" and a standard regional check variety, referred to as "Parris Island."

In Table 2, the seed color, cotyledon shape and characteristics of the fourth leaf of "41-122 RZ" is compared with "Actarus" and "Parris Island." RHS=Royal Horticultural Society colour chart code.

TABLE 2

Figure 2:
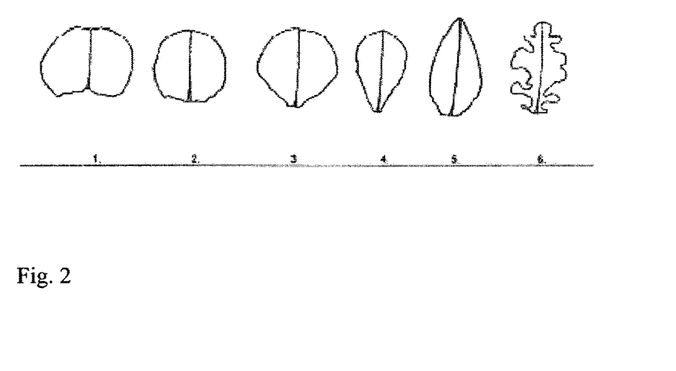
FIG. 2 is an illustration of six different shapes of the fourth leaf from a 20-day old seedling grown under optimal conditions.
Figure 3:
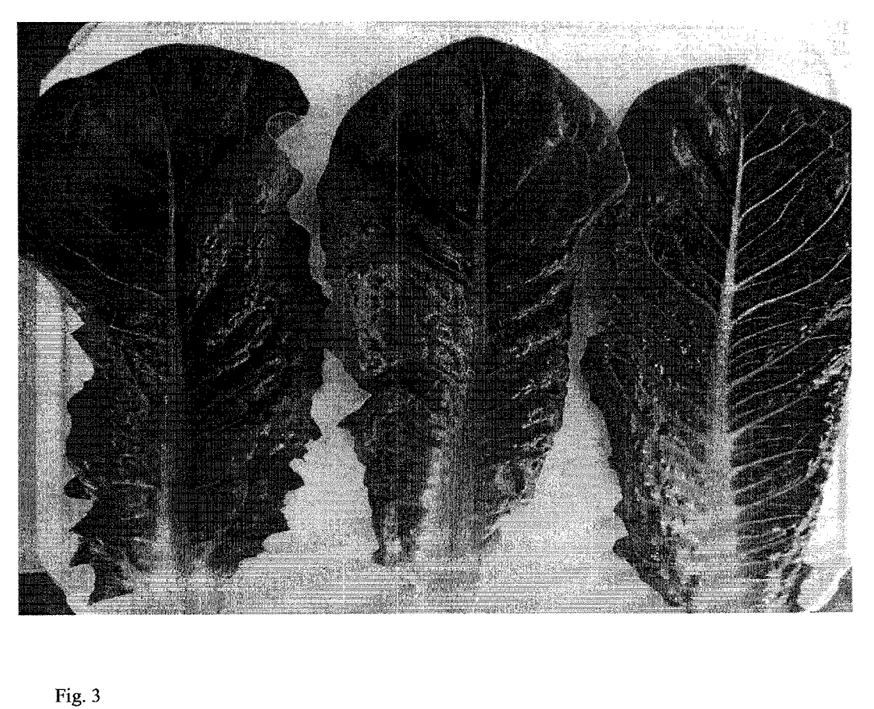
FIG. 3 shows a mature leaf of 41-122 RZ (right), as compared to variety Actarus (left) and variety Easala (middle).

| Character | "41-122 RZ" | "Actarus" | "Parris Island" |
|---|---|---|---|
| Plant Type | Romaine or Cos | Romaine or Cos | Romaine or Cos |
| Seed Color | White (Silver Gray) | White (Silver Gray) | White (Silver Gray) |
| Cotyledon Shape | Broad | broad | Intermediate |
| Shape of Fourth Leaf | No. 4 on FIG. 2 | No. 4 on FIG. 2 | No. 4 on FIG. 2 |
| Rolling of Fourth Leaf | Absent | Absent | Absent |
| Cupping of Fourth Leaf | Uncupped | Uncupped | Uncupped |
| Fourth Leaf Apical Margin | Entire | Entire | Entire |
| Undulation | Flat | Flat | Flat |

In Table 3, the mature leaf and head characteristics of "41-122 RZ" is compared with "Actarus" and "Parris Island."

TABLE 3

| Character | "41-122 RZ" | "Actarus" | "Parris Island" |
|---|---|---|---|
| Green Color | RHS 137B | RHS 137B | RHS 137A |
| Anthocyanin Distribution | Absent | Absent | Absent |
| Margin Incision Depth | Absent/Shallow | Absent/Shallow | Absent/Shallow |
| Margin Indentation | Shallowly Dentate | Shallowly Dentate | Shallowly Dentate |
| Undulations of the Apical Margin | Absent/Slight | Absent/Slight | Absent/Slight |
| Leaf Size | Large to Medium | Large to Medium | Large |
| Leaf Glossiness | Moderate | Moderate | Moderate to Dull |
| Leaf Blistering | Strong | Moderate | Moderate |
| Leaf Thickness | Thick | Intermediate | Intermediate to Thick |
| Trichomes | Absent (Smooth) | Absent (Smooth) | Absent (smooth) |
| Head Shape | Elongate | Elongate | Elongate |
| Head Size | Medium | Medium | Large |
| Head Firmness | Moderate | Moderate | Firm |
| Butt Shape | Rounded | Rounded | Rounded |
| Midrib | Prominently Raised | Prominently Raised | Prominently Raised |

In Table 4, the characteristics of the core and the bolter plant of "41-122 RZ" is compared with "Actarus" and "Parris Island."

TABLE 4

| Character | "41-122 RZ" | "Actarus" | "Parris Island" |
|---|---|---|---|
| Bolting Class | Very Slow | Very Slow | Slow |
| Bolter Leaves | Straight | Straight | Slightly Curved |
| Margin | Slightly Dentate | Dentate | Slightly Dentate |
| Color | RHS 137A | RHS 137A | RHS 137B |

TABLE 4-continued

| Character | "41-122 RZ" | "Actarus" | "Parris Island" |
|---|---|---|---|
| Terminal Inflorescence | Present | Present | Present |
| Lateral Shoots | Present | Present | Present |
| Basal Side Shoots | Present | Present | Present |

In an embodiment, the invention relates to lettuce plants that has all the morphological and physiological characteristics of the invention and have acquired said characteristics by introduction of the genetic information that is responsible for the characteristics from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that can be introduced by backcrossing, useful traits can be introduced directly into the plant of the invention, being a plant of lettuce variety 41-122 RZ, by genetic transformation techniques; and, such plants of lettuce variety 41-122 RZ that have additional genetic information introduced into the genome or that express additional traits by having the DNA coding there for introduced into the genome via transformation techniques, are within the ambit of the invention, as well as uses of such plants, and the making of such plants.

Genetic transformation may therefore be used to insert a selected transgene into the plant of the invention, being a plant of lettuce variety 41-122 RZ or may, alternatively, be used for the preparation of transgenes which can be introduced by backcrossing. Methods for the transformation of plants, including lettuce, are well known to those of skill in the art.

Vectors used for the transformation of lettuce cells are not limited so long as the vector can express an inserted DNA in the cells. For example, vectors comprising promoters for constitutive gene expression in lettuce cells (e.g., cauliflower mosaic virus 35S promoter) and promoters inducible by exogenous stimuli can be used. Examples of suitable vectors include pBI binary vector. The "lettuce cell" into which the vector is to be introduced includes various forms of lettuce cells, such as cultured cell suspensions, protoplasts, leaf sections, and callus. A vector can be introduced into lettuce cells by known methods, such as the polyethylene glycol method, polycation method, electroporation, *Agrobacterium*-mediated transfer, particle bombardment and direct DNA uptake by protoplasts. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target lettuce cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including a plant of lettuce variety 41-122 RZ.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations. Moreover, advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, *Agrobacterium* containing both armed and disarmed Ti genes can be used for transformation. In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells, including lettuce plant cells, is well known in the art (See, e.g., U.S. Pat. Nos. 7,250,560 and 5,563,055).

Transformation of plant protoplasts also can be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for lettuce plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins from lettuce (psaD, psaF, psaE, PC, FNR, atpC, atpD, cab, rbcS) (see U.S. Pat. No. 7,161,061), the CAB-1 promoter from lettuce (see U.S. Pat. No. 7,663,027), the promoter from maize prolamin seed storage protein (see U.S. Pat. No. 7,119,255), and other plant DNA virus promoters known to express in plant cells. A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wun1, or (5) chemicals such as methyl jasmonate, salicylic acid, or Safener. It may also be advantageous to employ organ-specific promoters.

Exemplary nucleic acids which may be introduced to the lettuce variety of this invention include, for example, DNA sequences or genes from another species, or even genes or sequences which originate with or are present in lettuce species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of lettuce variety 41-122 RZ. Non-limiting examples of particular genes and corresponding phenotypes one may choose to introduce into a lettuce plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat. No. 7,576,262, "Modified gene-silencing RNA and uses thereof.")

U.S. Pat. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above INCORPORATION BY REFERENCE section, are additionally cited as examples of U.S. patents that may concern transformed lettuce and/or methods of transforming lettuce or lettuce plant cells, and techniques from these US patents, as well as promoters, vectors, etc., may be employed in the practice of this invention to introduce exogenous nucleic acid sequence(s) into a plant of lettuce variety 41-122 RZ (or cells thereof), and exemplify some exogenous nucleic acid sequence(s) which can be introduced into a plant of lettuce variety 41-122 RZ (or cells thereof) of the invention, as well as techniques, promoters, vectors etc., to thereby obtain further plants of lettuce variety 41-122 RZ, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material comprises inter alia seeds of the claimed plant and parts of the plant that are involved in sexual reproduction. Such parts are for example selected from the group consisting of seeds, microspores, pollen, ovaries, ovules, embryo sacs and egg cells. In addition, the invention relates to propagation material comprising parts of the plant that are suitable for vegetative reproduction, for example cuttings, roots, stems, cells, protoplasts.

According to a further aspect thereof the propagation material of the invention comprises a tissue culture of the claimed plant. The tissue culture comprises regenerable cells. Such tissue culture can be derived from leaves, pollen, embryos, cotyledon, hypocotyls, meristematic cells, roots, root tips, anthers, flowers, seeds and stems. (See generally U.S. Pat. No. 7,041,876 on lettuce being recognized as a plant that can be regenerated from cultured cells or tissue).

Also, the invention comprehends methods for producing a seed of a "41-122 RZ"-derived lettuce plant comprising (a) crossing a plant of lettuce variety 41-122 RZ, representative seed of which having been deposited under NCIMB Accession No. NCIMB 41832, with a second lettuce plant, and (b) whereby seed of a "41-122 RZ"-derived lettuce plant form (e.g., by allowing the plant from the cross to grow to producing seed). Such a method can further comprise (c) crossing a plant grown from "41-122 RZ"-derived lettuce seed with itself or with a second lettuce plant to yield additional "41-122 RZ"-derived lettuce seed, (d) growing the additional "41-122 RZ"-derived lettuce seed of step (c) to yield additional "41-122 RZ"-derived lettuce plants, and (e) repeating the crossing and growing of steps (c) and (d) to generate further "41-122 RZ"-derived lettuce plants.

The invention additionally provides a method of introducing a desired trait into a plant of lettuce variety 41-122 RZ comprising: (a) crossing a plant of lettuce variety 41-122 RZ, representative seed of which having been deposited under NCIMB Accession No. NCIMB 41832, with a second lettuce plant that comprises a desired trait to produce F1 progeny; (b) selecting an F1 progeny that comprises the desired trait; (c) crossing the selected F1 progeny with a plant of lettuce variety 41-122 RZ, to produce backcross progeny; (d) selecting backcross progeny comprising the desired trait and the physiological and morphological characteristic of a plant of lettuce variety 41-122 RZ; and, optionally, (e) repeating steps (c) and (d) one or more times in succession to produce selected fourth or higher backcross progeny that comprise the desired trait and all of the physiological and morphological characteristics of a plant of lettuce variety 41-122 RZ, when grown in the same environmental conditions. The invention, of course, includes a lettuce plant produced by this method.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred. When a plant of lettuce variety 41-122 RZ, representative seed of which having been deposited under NCIMB Accession No. NCIMB 41832, is used in backcrossing, offspring retaining the combination of traits including resistance against downy mildew (*Bremia lactucae*), leaves with a solid main vein, narrow base leaves, and thick, strongly blistered, mature leaves are progeny within the ambit of the invention. Backcrossing methods can be used with the present invention to improve or introduce a characteristic into a plant of the invention, being a plant of lettuce variety 41-122 RZ. See, e.g., U.S. Pat. No. 7,705,206 (incorporated herein by reference consistent with the above INCORPORATION BY REFERENCE section), for a general discussion relating to backcrossing.

The invention further involves a method of determining the genotype of a plant of lettuce variety 41-122 RZ, representative seed of which has been deposited under NCIMB Accession No. NCIMB 41832, or a first generation progeny thereof, comprising obtaining a sample of nucleic acids from said plant and detecting in said nucleic acids a plurality of polymorphisms. This method can additionally comprise the step of storing the results of detecting the plurality of polymorphisms on a computer readable medium. The plurality of polymorphisms are indicative of and/or give rise to the expression of the morphological and physiological characteristics of lettuce variety 41-122 RZ.

Lettuce leaves are sold in packaged form, including without limitation as pre-packaged lettuce salad or as lettuce heads. Mention is made of U.S. Pat. No. 5,523,136, incorporated herein by reference consistent with the above INCORPORATION BY REFERENCE section, which provides packaging film, and packages from such packaging film, including such packaging containing leafy produce, and methods for making and using such packaging film and packages, which are suitable for use with the lettuce leaves of the invention. Thus, the invention comprehends the use of and methods for making and using the leaves of the lettuce plant of the invention, as well as leaves of lettuce plants derived from the invention. The invention further relates to a container comprising one or more plants of the invention, or one or more lettuce plants derived from a plant of the invention, in a growth substrate for harvest of leaves from the plant in a domestic environment. This way the consumer can pick very fresh leaves for use in salads. More generally, the invention includes one or more plants of the invention or one or more plants derived from lettuce of the invention, wherein the plant is in a ready-to-harvest condition, including with the consumer picking his own, and further including a container comprising one or more of these plants.

The invention is further described by the following numbered paragraphs:

1. Lettuce plant exhibiting a combination of traits including resistance against downy mildew (*Bremia lactucae* Regel), leaves with a solid main vein, narrow base leaves, and thick, strongly blistered, dark green mature leaves, representative seed of which having been deposited under NCIMB Accession No. 41832.

2. Lettuce plant exhibiting a combination of traits including resistance against downy mildew (*Bremia lactucae* Regel), leaves with a solid main vein, narrow base leaves, thick, strongly blistered, dark green mature leaves, a short core, absence of fringe burn, absence of tipburn, no undulation of the fourth leaf, and very slow bolting, representative seed of which having been deposited under NCIMB Accession No. 41832.

3. Lettuce plant designated 41-122 RZ, representative seed of which having been deposited under NCIMB Accession No. 41832.

4. A seed of the plant of paragraph 1.

5. Parts of the plant of paragraph 1, wherein said parts of the plant are suitable for sexual reproduction.

6. Parts of the plant of paragraph 5, said parts selected from the group consisting of microspores, pollen, ovaries, ovules, embryo sacs and egg cells.

7. Parts of the plant of paragraph 1, wherein said parts of the plant are suitable for vegetative reproduction.

8. Parts of paragraph 7, said parts selected from the group consisting of cuttings, roots, stems, cells and protoplasts.

9. A tissue culture of regenerable cells from the lettuce plant of paragraph 1.

10. A tissue culture of paragraph 9, wherein said cells or protoplasts of the tissue culture which are derived from a tissue selected from the group consisting of leaves, pollen, embryos, cotyledon, hypocotyls, meristematic cells, roots, root tips, anthers, flowers, seeds and stems.

11. Progeny of a lettuce plant of paragraph 1.

12. Progeny of paragraph 11, wherein said progeny is produced by sexual or vegetative reproduction of said lettuce plant, and wherein said progeny exhibits a combination of traits including resistance against downy mildew (*Bremia lactucae*), leaves with a solid main vein, narrow base leaves, and thick, strongly blistered, dark green mature leaves.

13. Progeny of a lettuce plant of paragraph 3, having all the morphological and physiological characteristics of the lettuce plant of paragraph 3, representative seed of which having been deposited under NCIMB Accession No. 41832 wherein as found in lettuce variety 41-122 RZ, representative seed of which having been deposited under NCIMB Accession No. 41832.

14. Progeny of a lettuce plant of paragraph 1, representative seed of which having been deposited under NCIMB Accession 41832, and is modified in one or more other characteristics.

15. Progeny of paragraph 14, wherein the modification is effected by mutagenesis.

16. Progeny of paragraph 14, wherein the modification is effected by transformation with a transgene.

17. A method of producing a hybrid lettuce seed comprising crossing a first parent lettuce plant with a second parent lettuce plant and harvesting the resultant hybrid lettuce seed, wherein said first parent lettuce plant or said second parent lettuce plant is the lettuce plant of paragraph 1.

18. A method of producing a lettuce cultivar containing a combination of traits including resistance against downy mildew (*Bremia lactucae*), leaves with a solid main vein, narrow base leaves, and thick, strongly blistered, dark green mature leaves, comprising: crossing a mother lettuce plant with a father lettuce plant to produce a hybrid seed; growing said hybrid seed to produce a hybrid plant; selfing said hybrid seed to produce F2 progeny seed; selecting said F2-plants for exhibiting resistance against downy mildew (*Bremia lactucae*), leaves with a solid main vein, narrow base leaves, and thick, strongly blistered, dark green mature leaves, and, selfing said selected F2-plants to produce F3 progeny seed; selecting F3-plants for exhibiting resistance against downy mildew (*Bremia lactucae*), leaves with a solid main vein, narrow base leaves, and thick, strongly blistered, dark green mature leaves, optionally followed by more selfing and selection steps.

19. A method for producing lettuce leaves as a fresh vegetable comprising packaging leaves of a plant of paragraph 1.

20. A method for producing lettuce leaves as a processed food comprising processing leaves of a plant of paragraph 1.

21. One or more lettuce plants of paragraph 1, in a container, for harvest of leaves.

22. Lettuce plant having morphological and/or physiological characteristics of a lettuce plant, representative seed of which having been deposited under NCIMB Accession No. 41832.

23. Lettuce plant of paragraph 22 having all the morphological and physiological characteristics of the lettuce plant, representative seed of which having been deposited under NCIMB Accession No. 41832.

24. A method of introducing a desired trait into a plant of lettuce variety 41-122 RZ comprising: (a) crossing a plant of lettuce variety 41-122 RZ, representative seed of which having been deposited under NCIMB Accession No. NCIMB 41832, with a second lettuce plant that comprises the desired trait to produce F1 progeny; (b) selecting an F1 progeny that comprises the desired trait; (c) crossing the selected F1 progeny with a plant of lettuce variety 41-122 RZ, to produce backcross progeny and (d) selecting backcross progeny comprising the desired trait and the physiological and morphological characteristic of a plant of lettuce variety 41-122 RZ, when grown in the same environmental conditions.

25. The method of paragraph 24 further comprising (e) repeating steps (c) and (d) one or more times in succession to produce selected fourth or higher backcross progeny that comprise the desired trait and all of the physiological and morphological characteristics of a plant of lettuce variety 41-122 RZ, when grown in the same environmental conditions.

26. A lettuce plant produced by the method of paragraph 24 or 25.

27. A method for producing a seed of a 41-122 RZ-derived lettuce plant comprising (a) crossing a plant of lettuce variety 41-122 RZ, representative seed of which having been deposited under NCIMB Accession No. NCIMB 41832, with a second lettuce plant, and (b) whereby seed of a 41-122 RZ-derived lettuce plant form.

28. The method of paragraph 27 further comprising (c) crossing a plant grown from 41-122 RZ-derived lettuce seed with itself or with a second lettuce plant to yield additional 41-122 RZ-derived lettuce seed, (d) growing the additional 41-122 RZ-derived lettuce seed of step (c) to yield additional 41-122 RZ-derived lettuce plants, and (e) repeating the crossing and growing of steps (c) and (d) to generate further 41-122 RZ-derived lettuce plants.

29. A method of determining the genotype of a plant of lettuce variety 41-122 RZ, representative seed of which has been deposited under NCIMB Accession No. NCIMB 41832, or a first generation progeny thereof, comprising obtaining a sample of nucleic acids from said plant and detecting in said nucleic acids a plurality of polymorphisms, wherein the plurality of polymorphisms are indicative of and/or give rise to the expression of the morphological and physiological characteristics of lettuce variety 41-122 RZ.

30. The method of paragraph 29 additionally comprising the step of storing the results of detecting the plurality of polymorphisms on a computer readable medium, or transmitting the results of detecting the plurality of polymorphisms.

Having thus described in detail preferred embodiments of the present invention, it is to be understood that the invention is not to be limited to particular details set forth in the above description as many apparent variations thereof are possible without departing from the spirit or scope of the present invention.

What is claimed is:

1. A lettuce plant exhibiting a combination of traits including resistance against downy mildew (*Bremia lactucae* Regel), leaves with a solid main vein, narrow base leaves, and thick, strongly blistered, dark green mature leaves, representative seed of which having been deposited under NCIMB Accession No. 41832.

2. The lettuce plant of claim 1 further exhibiting a combination of traits including a short core, absence of fringe burn, absence of tipburn, no undulation of the fourth leaf, and very slow bolting.

3. A seed of the plant of claim 1.

4. Parts of the plant of claim 1, wherein said parts of the plant are suitable for sexual reproduction or
wherein said parts of the plant are suitable for sexual reproduction and wherein said parts are selected from the group consisting of microspores, pollen, ovaries, ovules, embryo sacs and egg cells or
wherein said parts of the plant are suitable for vegetative reproduction or
wherein said parts of the plant are suitable for vegetative reproduction and wherein said parts selected from the group consisting of cuttings, roots, stems, cells and protoplasts.

5. A tissue culture of regenerable cells from the lettuce plant of claim 1, optionally wherein said cells or protoplasts of the tissue culture are derived from a tissue selected from the group consisting of leaves, pollen, embryos, cotyledon, hypocotyls, meristematic cells, roots, root tips, anthers, flowers, seeds and stems.

6. Progeny of a lettuce plant of claim 1, wherein said progeny exhibits a combination of traits including resistance against downy mildew (*Bremia lactucae*), leaves with a solid main vein, narrow base leaves, and thick, strongly blistered, dark green mature leaves.

7. Progeny as claimed in claim 6, wherein said progeny is produced by sexual or vegetative reproduction of said lettuce plant.

8. Progeny of a lettuce plant of claim 1, representative seed of which having been deposited under NCIMB Accession 41832, wherein the progeny exhibits the combination of traits of the lettuce plant of claim 1, and is further modified in one or more other characteristics.

9. Progeny as claimed in claim 8, wherein the modification is effected by mutagenesis or wherein the modification is effected by transformation with a transgene.

10. A method of producing a hybrid lettuce seed comprising crossing a first parent lettuce plant with a second parent lettuce plant and harvesting the resultant hybrid lettuce seed, wherein said first parent lettuce plant or said second parent lettuce plant is the lettuce plant of claim 1 or
a method of producing a lettuce cultivar containing a combination of traits including resistance against downy mildew (*Bremia lactucae*), leaves with a solid main vein, narrow base leaves, and thick, strongly blistered, dark green mature leaves, comprising: crossing a mother lettuce plant with a father lettuce plant to produce a hybrid seed; growing said hybrid seed to produce a hybrid plant; selfing said hybrid seed to produce F2 progeny seed; selecting said F2-plants for exhibiting resistance against downy mildew (*Bremia lactucae*), leaves with a solid main vein, narrow base leaves, and thick, strongly blistered, dark green mature leaves, and, selfing said selected F2-plants to produce F3 progeny seed; selecting F3-plants for exhibiting resistance against downy mildew (*Bremia lactucae*), leaves with a solid main vein, narrow base leaves, and thick, strongly blistered, dark green mature leaves, optionally followed by more selfing and selection steps.

11. A method for producing lettuce leaves as a fresh vegetable comprising packaging leaves of a plant of claim 1.

12. A method for producing lettuce leaves as a processed food comprising processing leaves of a plant of claim 1.

13. A lettuce plant having morphological and/or physiological characteristics of a lettuce plant, representative seed of which having been deposited under NCIMB Accession No. 41832, and wherein said lettuce plant exhibits a combination of traits including resistance to downy mildew (*Bremia Lactucae* Regel), leaves with a solid main vein, narrow base leaves, and thick strongly blistered, dark green mature leaves.

14. The lettuce plant of claim 13 having all the morphological and physiological characteristics of the lettuce plant, representative seed of which having been deposited under NCIMB Accession No. 41832.

15. A method of introducing a desired trait into a plant of lettuce variety 41-122 RZ comprising: (a) crossing a plant of lettuce variety 41-122 RZ, representative seed of which having been deposited under NCIMB Accession No. NCIMB 41832, with a second lettuce plant that comprises the desired trait to produce F1 progeny; (b) selecting an F1 progeny that comprises the desired trait; (c) crossing the selected F1 progeny with a plant of lettuce variety 41-122 RZ, to produce backcross progeny and (d) selecting backcross progeny comprising the desired trait and all of the physiological and morphological characteristics of a plant of lettuce variety 41-122 RZ, when grown in the same environmental conditions.

16. The method of claim 15 further comprising (e) repeating steps (c) and (d) one or more times in succession to produce selected fourth or higher backcross progeny that comprise the desired trait and all of the physiological and morphological characteristics of a plant of lettuce variety 41-122 RZ, when grown in the same environmental conditions.

17. A lettuce plant produced by the method of claim 15.

18. A method for producing a seed of a 41-122 RZ-derived lettuce plant comprising (a) crossing a plant of lettuce variety 41-122 RZ, representative seed of which having been deposited under NCIMB Accession No. NCIMB 41832, with a second lettuce plant, and (b) whereby seed of a 41-122 RZ-derived lettuce plant form.

19. The method of claim 18 further comprising (c) crossing a plant grown from 41-122 RZ-derived lettuce seed with itself or with a second lettuce plant to yield additional 41-122 RZ-derived lettuce seed, (d) growing the additional 41-122 RZ-derived lettuce seed of step (c) to yield additional 41-122 RZ-derived lettuce plants, and (e) repeating the crossing and growing of steps (c) and (d) to generate further 41-122 RZ-derived lettuce plants.

20. A method of determining the genotype of a plant of lettuce variety 41-122 RZ, representative seed of which has been deposited under NCIMB Accession No. NCIMB 41832, or a first generation progeny thereof, comprising obtaining a sample of nucleic acids from said plant and detecting in said nucleic acids a plurality of polymorphisms, wherein the plurality of polymorphisms are indicative of and/or give rise to the expression of the morphological and physiological characteristics of lettuce variety 41-122 RZ and
optionally additionally comprising the step of storing the results of detecting the plurality of polymorphisms on a computer readable medium, or transmitting the results of detecting the plurality of polymorphisms.

21. A lettuce plant designated 41-122 RZ, representative seed of which having been deposited under NCIMB Accession No. 41832.

22. Progeny of a lettuce plant designated 41-122 RZ, representative seed of which having been deposited under NCIMB Accession No. 41832, having all the morphological and physiological characteristics of the lettuce plant designated 41-122 RZ.

23. A lettuce plant exhibiting a combination of traits including resistance against downy mildew (*Bremia lactucae* Regel), leaves with a solid main vein, narrow base leaves, and thick, strongly blistered, dark green mature leaves and having genetic material for so exhibiting the combination of traits; wherein the genetic information is as contained in a plant, representative seed of which having been deposited under NCIMB Accession No. 41832.

\* \* \* \* \*